(12) United States Patent
Simpson et al.

(10) Patent No.: US 7,419,477 B2
(45) Date of Patent: Sep. 2, 2008

(54) CATHETERIZATION METHOD USING PROXIMAL ARTICULATION AND PRE-FORMED DISTAL END

(75) Inventors: John A. Simpson, Carlsbad, CA (US); Robert C. Hayzelden, Canyon Lake, CA (US); Wade A. Bowe, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 563 days.

(21) Appl. No.: 10/855,544

(22) Filed: May 27, 2004

(65) Prior Publication Data
US 2004/0220520 A1 Nov. 4, 2004

Related U.S. Application Data

(62) Division of application No. 10/105,087, filed on Mar. 22, 2002, now Pat. No. 6,869,414.

(51) Int. Cl.
*A61M 31/00* (2006.01)
*A61M 37/00* (2006.01)
*A61B 18/18* (2006.01)

(52) U.S. Cl. .................. 604/95.04; 606/41; 600/585

(58) Field of Classification Search ............ 606/41, 606/45–50; 604/95.04, 93.01, 95.01; 600/585, 600/433–435
See application file for complete search history.

(56) References Cited

U.S. PATENT DOCUMENTS

| 5,195,968 | A | 3/1993 | Lundquist et al. | |
|---|---|---|---|---|
| 5,378,234 | A * | 1/1995 | Hammerslag et al. | .... 604/95.04 |
| 5,389,090 | A | 2/1995 | Fischell et al. | |
| 6,059,778 | A | 5/2000 | Sherman | |
| 6,066,126 | A | 5/2000 | Li et al. | |
| 6,096,036 | A | 8/2000 | Bowe et al. | |
| 6,179,809 | B1 * | 1/2001 | Khairkhahan et al. | .... 604/95.04 |
| 6,198,974 | B1 | 3/2001 | Webster, Jr. | |
| 6,270,496 | B1 * | 8/2001 | Bowe et al. | ................. 606/41 |
| 6,280,433 | B1 | 8/2001 | McIvor et al. | |
| 6,408,214 | B1 | 6/2002 | Williams et al. | |
| 6,530,914 | B1 | 3/2003 | Mickley | |
| 6,585,718 | B2 * | 7/2003 | Hayzelden et al. | .......... 604/523 |
| 6,628,976 | B1 * | 9/2003 | Fuimaono et al. | ........... 600/374 |
| 6,795,721 | B2 * | 9/2004 | Coleman et al. | ........... 600/374 |

* cited by examiner

*Primary Examiner*—Michael Peffley
(74) *Attorney, Agent, or Firm*—Hollingsworth & Funk, LLC

(57) ABSTRACT

Methods of using a catheter involve providing a sheath comprising a proximal region, a deflection region, a distal-end region including a shapeable region, an anchor region defined between the deflection region and the shapeable region, and a longitudinal axis. The method also involves imparting a pre-established shape to the shapeable region. The method further involves applying axial force in a proximal direction at the anchor region so as to cause the deflection region to deflect relative to the longitudinal axis while the pre-established shape imparted to the shapeable region of the sheath is substantially maintained.

18 Claims, 7 Drawing Sheets

RELAXED CONFIGURATION

STEERED CONFIGURATION

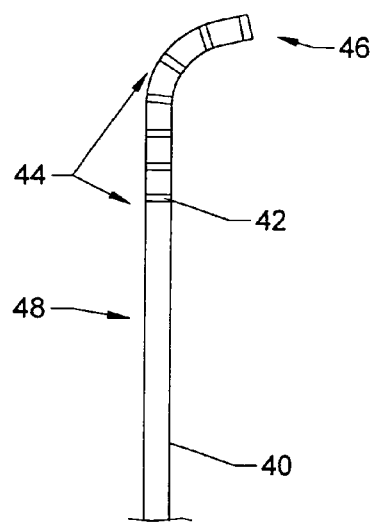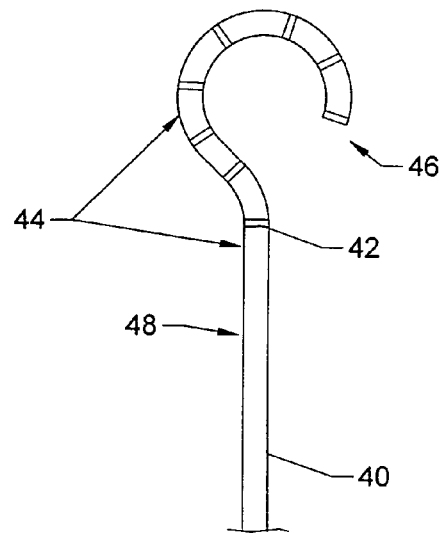
Fig. 3A                Fig. 3B
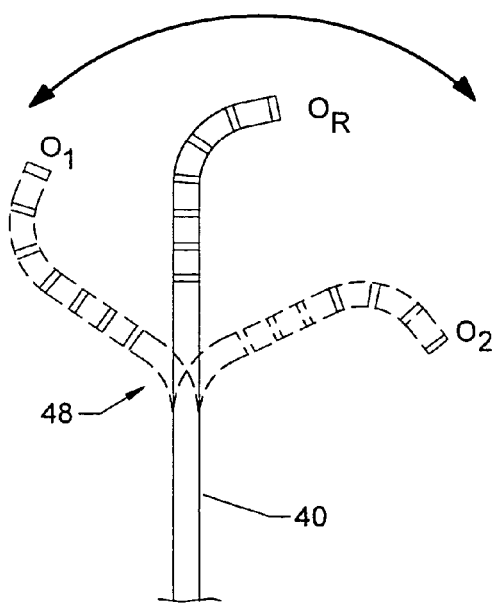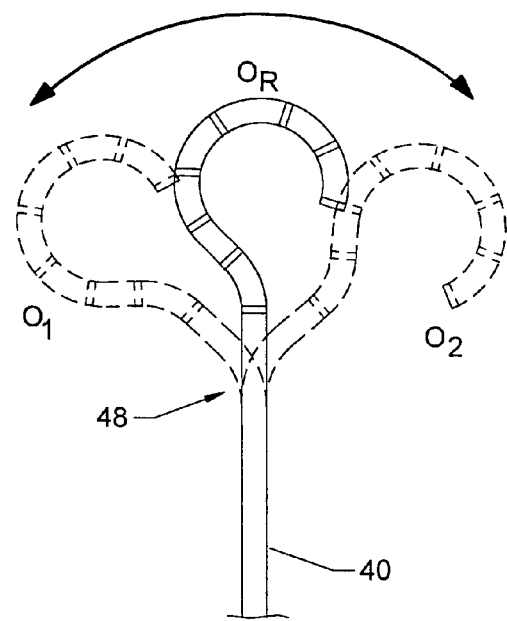
Fig. 4A                Fig. 4B

CATHETERIZATION METHOD USING PROXIMAL ARTICULATION AND PRE-FORMED DISTAL END

RELATED PATENT DOCUMENTS

This application is a divisional of U.S. patent application Ser. No. 10/105,087, filed on Mar. 22, 2002, now U.S. Pat. No. 6,869,414, to which priority is claimed under 35 U.S.C. § 120, and which is incorporated herein by reference.

FIELD OF THE INVENTION

The present invention relates generally to steerable catheters and, more particularly, to methods involving a steerable catheter employing a pre-formed distal end section and a proximal steering mechanism.

BACKGROUND OF THE INVENTION

Mapping and ablation catheters are well-established technologies that allow the physician to locate and treat damaged cardiac tissue. Presently, a considerable amount of time is often spent by the physician when manipulating such catheters within cardiac structures, such as the right atrium, simply trying to locate an anatomical feature of interest, such as the coronary sinus ostium.

A pre-shaped guiding catheter is typically used to blindly locate the coronary sinus ostium, but this endeavor is complicated by the fact that the location of the coronary sinus ostium may vary appreciably from one patient to another, especially among patients with diseased hearts. Oftentimes, the clinician is entirely unable to locate the coronary sinus ostium using the guiding catheter, and must resort to finding the ostium by "mapping" (interpreting localized bipolar waveforms) using an electrophysiological (EP) catheter and an ECG monitor. After the ostium is located, a guiding catheter or sheath is typically used to inject radiographic contrast media into the coronary sinus to highlight the associated venous system, and then a pacing lead is installed within one of the coronary branches.

Steerability is also important for ablation catheter implementations. In many cases, ablation of the damaged tissue can restore the correct operation of the heart. Ablation can be performed, for example, by percutaneous ablation, a procedure in which a catheter is percutaneously introduced into the patient and directed through an artery to the atrium or ventricle of the heart to perform single or multiple diagnostic, therapeutic, and/or surgical procedures. In such a case, an ablation procedure is used to destroy the tissue causing the arrhythmia in an attempt to remove the electrical signal irregularities or create a conductive tissue block to restore normal heartbeat or at least an improved heartbeat. Successful ablation of the conductive tissue at the arrhythmia initiation site usually terminates the arrhythmia or at least moderates the heart rhythm to acceptable levels. A widely accepted treatment for arrhythmia involves the application of radio frequency (RF) energy to the conductive tissue.

By way of example, a procedure to address atrial fibrillation, referred to as Cox's Maze procedure, involves the development of continuous atrial incisions to prevent atrial re-entry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate electrophysiological (EP) catheter system having enhanced steering and shape adjustment capabilities.

Steerable conventional mapping and ablation catheter systems are typically configured to allow the profile of the distal end of the catheter to be manipulated from a location outside the patient's body. The contours of pre-shaped diagnostic catheters, for example, are generally fixed, and this is typically achieved in production by constraining the distal end within a shaping fixture while warming them until they assume the intended shape (i.e., by "heat setting" their polymer shaft). The shape of steerable mapping catheters, on the other hand, can be altered by the user simply by applying tension to one or more internal steering tendons affixed to a distal-end tip of the catheter. However, most steerable mapping catheters are generally straight when no tension is applied to the tendons. When steered, the distal end of such steerable catheters assumes a semicircular arc or full circular shape whose radius of curvature depends upon the amount of tension applied to the steering tendon.

FIGS. 1 and 2 illustrate a conventional steerable catheter in a relaxed configuration and a steered configuration, respectively. Catheter 20 is shown to include a number of band electrodes 22 and a tip electrode 24. As can be seen in FIG. 1, catheter 20 maintains a relatively straight profile while in a relaxed configuration.

FIG. 2 illustrates the catheter 20 of FIG. 1 in a steered configuration. According to this and other conventional steerable catheter implementations, catheter 20 has a distal end that assumes a semicircular arc or a fully circular shape when tension is applied to the catheter's steering tendon(s). The circular arc of catheter 20, when in its steered configuration, develops a shape whose radius, R, of curvature depends upon the amount of tension applied to the distal end vis-à-vis the steering tendon(s). It will be appreciated by those skilled in the art that enhanced steering capabilities are often required over and above those offered by conventional steerable catheters, such as those of the type depicted in FIGS. 1 and 2, for locating (e.g., such as by mapping) certain anatomical features and performing an ablation technique once such anatomical features have been located and accessed.

There is a need for an improved steerable catheter having enhanced steering capabilities for mapping and ablation applications. There exists a further need for such a catheter that provides for increased lumen space for accommodating larger payloads and one that resists deformation after repeated steering. The present invention fulfills these and other needs, and addresses other deficiencies of prior art implementations.

SUMMARY OF THE INVENTION

The present invention is directed to methods involving manipulation of a catheter or sheath. According to one embodiment, a method involves providing a catheter comprising a proximal region, a pre-formed region at a distal end of the catheter, a deflection mechanism proximal to the pre-formed region, a deflection region proximal to the deflection mechanism, and a longitudinal axis. The method also involves applying axial force in a proximal direction to the deflection mechanism, the axial force causing the deflection region to deflect relative to a longitudinal axis of the proximal region of the catheter while a pre-formed shape of the pre-formed region is substantially maintained. The method further involves resisting axial compression along the longitudinal axis at the deflection region resulting from application of the axial force.

According to another embodiment, a method involves providing a sheath comprising a proximal region, a deflection region, a distal-end region including a shapeable region, an anchor region defined between the deflection region and the shapeable region, and a longitudinal axis. The method also involves imparting a pre-established shape to the shapeable region. The method further involves applying axial force in a proximal direction at the anchor region so as to cause the deflection region to deflect relative to the longitudinal axis while the pre-established shape imparted to the shapeable region of the sheath is substantially maintained.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 3A is a depiction of a catheter employing a proximal steering mechanism and pre-shaped distal end in accordance with an embodiment of the present invention, the catheter shown in a relaxed configuration;

FIG. 3B is a depiction of a catheter employing a proximal steering mechanism and looped pre-shaped distal end in accordance with another embodiment of the present invention, the catheter shown in a relaxed configuration;

FIG. 4A is a depiction of the catheter of FIG. 3A shown in several steered configurations;

FIG. 4B is a depiction of the catheter of FIG. 3B shown in several steered configurations;

Figure 1:
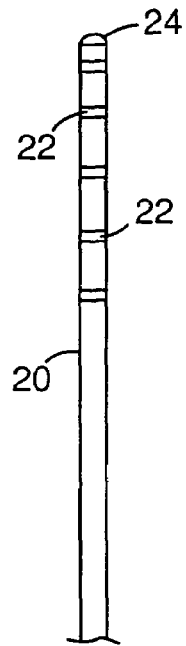
FIG. 1 is a depiction of a catheter employing a prior art steering mechanism, the catheter shown in a relaxed configuration.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Referring now to the drawings, and in particular to FIG. 3A, there is illustrated a catheter implemented in accordance with an embodiment of the present invention. The catheter 40 advantageously employs a pre-shaped distal section in combination with a deflectable proximal section which advantageously provides for controlled articulation of the catheter 40 without significantly altering the distal section's predetermined shape. In accordance with this embodiment, catheter 40 is shown to include a pre-shaped section 44 extending from a distal tip 46 of the catheter 40 toward a deflection section 48. The deflection section 48 provides for controlled articulation of the pre-shaped section 44 and distal tip 46 for steering the catheter 40 through vasculature and cardiac structures and for dynamically adjusting the overall contour of the catheter 40 during use. The pre-shaped section 44 and distal tip 46 are preferably formed of a resilient material such that the pre-formed shape of the various catheter sections can effectively be straightened when the catheter 40 is inserted into a patient's vasculature or other constraining tissue structure.

A catheter 40 implemented in accordance with the present invention may be used in many applications, such as in mapping or ablation applications. If catheter 40 is equipped with thermal sensors, for example, catheter 40 can be used to generate long, continuous lesions for the treatment of atrial fibrillation or atrial flutter.

An articulating catheter 40 in accordance with the present invention may be implemented in a variety of forms, such as in the form of an electrophysiological (EP) mapping catheter having multiple band electrodes 42. The band electrodes 42 disposed at the distal-end region of catheter 40 are used to collect localized ECG signals for the specialized purpose of locating the coronary sinus. It is readily appreciated by those skilled in the art that the articulating catheter of the present invention can also be used to deliver radio frequency (RF) energy to locally ablate cardiac tissue and thereby alter its inherent electrical conduction.

By way of further example, an articulating catheter 40 employing a pre-shaped distal section 44 and deflectable proximal section 48 may be used within the right atrium for mapping purposes to positively locate the ostium of the coronary sinus. It is well understood in the art that this activity is known to be particularly challenging within hearts where the anatomy has been distorted by chronic disease, such as congestive heart failure (CHF) or atrial fibrillation (AF). It is necessary, for example, to specifically locate the coronary sinus when implanting one of the pacemaker leads for synchronized dual-chamber pacing CHF patients. A shape-adjustable catheter implemented according to the principles of the present invention can be used to efficiently locate the coronary sinus and other anatomical features of interest.

In accordance with a further illustrative example, an alternate distal configuration of the catheter 40 is illustrated in FIG. 3B. The combination of a pre-shaped distal portion 44 and a deflectable proximal section 48 implemented in catheter 40 may be useful within the left atrium for accurately positioning an array of ablation electrodes around the ostia of one or more of the pulmonary veins in order to produce bi-directional conduction block. It is considered necessary to create such block often when treating AF patients using RF ablation to less-invasively emulate the established open heart surgical procedure commonly known as Cox's Maze procedure.

The pre-shaped distal portion 44 in the configuration of FIG. 3B includes a substantially circular or semi-circular loop. The band electrodes 42 deployed at the pre-shaped distal portion are thereby arrayed in a shape that is particularly suited for creating a conduction block in one or more pulmonary veins.

An important advantage provided by an articulating catheter 40 implemented in accordance with the principles of the present invention concerns a significantly increased lumen space within the catheter 40 which facilitates an increased number of electrical conductors and other catheter elements housed within the catheter 40 in comparison to prior art implementations. By way of example, a catheter 40 configured for ablation applications in accordance with the present invention may employ numerous band electrodes 42 (e.g., 6 or 12 electrodes), each bearing several individually insulated wires for power delivery and temperature measurement. In one such configuration, catheter 40 provides sufficient lumen space to accommodate numerous electrical wires (e.g., typically between 15-30 wires), a pre-shaped member situated at the distal section of catheter 40, two tendon wires, a steering ribbon, and an anchor band, all while maintaining a catheter outer diameter of 7 French (2.3 mm). Those skilled in the art will readily appreciate that providing sufficient lumen space for such payload presents a significant design challenge, which is solved by implementing a catheter 40 consistent with the principles of the present invention.

Returning to the discussion of FIGS. 3A and 4A, FIG. 3A illustrates an embodiment of catheter 40 in a relaxed configuration. As is depicted in FIG. 3A, the configuration of catheter 40 in a relaxed state is significantly different from the relaxed configuration of prior art catheter 20 depicted in FIG. 1.

FIG. 4A depicts catheter 40 in several steered configurations. For example, the pre-shaped section 44 may be selectively deflected from its relaxed orientation, $O_R$, about a pivot point defined by proximal deflection section 48. Pre-shaped section 44 may, for example, be deflected about proximal deflection section 48 in a direction toward the longitudinal axis of the proximal section of catheter 40, as is depicted at steered orientation, $O_1$. Also, the pre-shaped section 44 may be deflected toward and beyond a plane normal to the longitudinal axis of the proximal section of catheter 40, as is depicted at steered orientation, $O_2$.

By way of further example, FIG. 4B shows steered configurations for an articulated catheter 40 having a distal loop as seen in FIG. 3B. $O_R$ is a relaxed orientation, and $O_1$ and $O_2$ are deflected orientations similar to those orientations described with respect to FIG. 4A.

Figure 2:
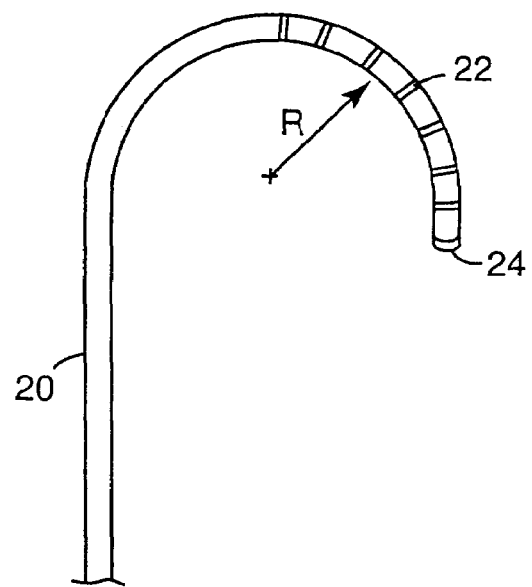
FIG. 2 is a depiction of the catheter of FIG. 1 shown in a steered configuration.

As can clearly be seen in FIGS. 4A and 4B, the distal portion of catheter 40 may be deflected at selected deflection angles relative to proximal deflection section 48 without significantly altering the predetermined shape of the distal section of catheter 40. In contrast, the steered configuration of prior art catheter 20 depicted in FIG. 2 illustrates significant alteration of the distal section of prior art catheter 20 in response to deflection forces exerted at the distal end 24 of catheter 20.

Figure 5:
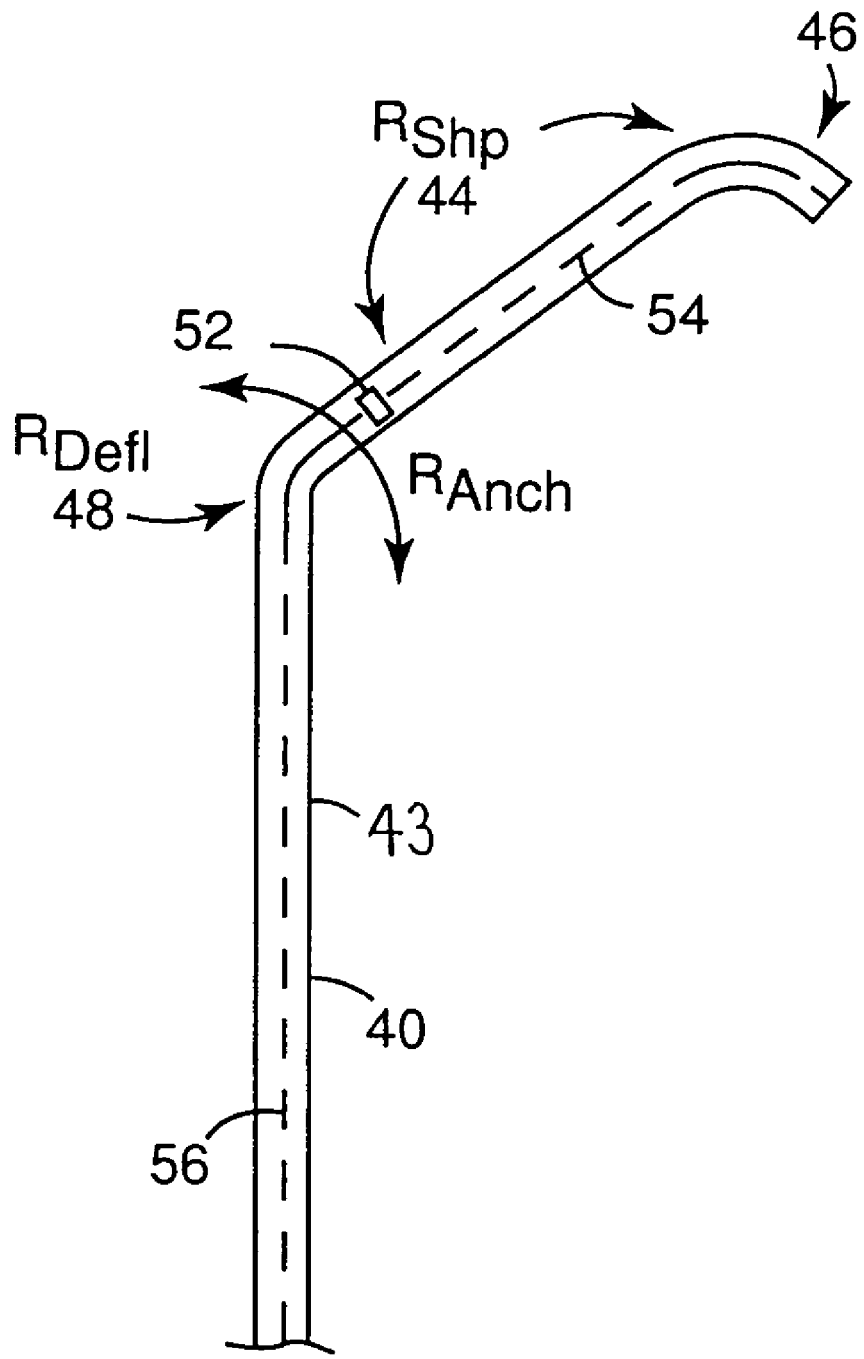
FIG. 5 is a depiction of a catheter employing a proximal steering mechanism and pre-shaped distal end in accordance with an embodiment of the present invention.

FIG. 5 is an illustration of an embodiment of the present invention in which an anchor region, $R_{anch}$, is shown to be located distal to a deflection region, $R_{defl}$, and proximal to a pre-shaped region, $R_{shp}$. A steering mechanism 56 extends from a proximal section 43 of catheter 40 to an anchor band 52 located at the anchor region, $R_{anch}$. A pre-shaped member 54 extends from the anchor band 52 through the pre-shaped region, $R_{shp}$. Preferably, pre-shaped member 54 is secured at the distal tip 46 of catheter 40. By appropriately actuating steering mechanism 56, tensile and torquing forces are imparted to anchor band 52 to cause pre-shaped region, $R_{shp}$, to deflect about the deflection region, $R_{defl}$, as will be discussed in greater detail hereinbelow.

The pre-shaped region, $R_{shp}$, takes on a shape consistent with that of pre-shaped member 54. The pre-formed shape of the pre-shaped region, $R_{shp}$, may have any form which generally conforms to the contour of the anatomical feature of interest. For example, the pre-shaped member 54 may have a contour that conforms to a biological cavity containing tissue to be ablated. It is understood that the configuration of pre-shaped region, $R_{shp}$, has been simplified for purposes of clarity, and that pre-shaped region, $R_{shp}$, may take various simple and complex forms. For example, the substantially straight portion of the pre-shaped region, $R_{shp}$, may instead have a simple or complex curved contour that follows that of pre-shaped member 54. The pre-shaped section, $R_{shp}$, may, for example, have a form that facilitates treatment of atrial fibrillation in that its shape allows for the distal portion of catheter 40 to be easily inserted into the atrium of the heart. The pre-formed member 54 employed in combination with proximal deflection region, $R_{defl}$, and steering mechanism 56 provides for a shape-adjustable, steerable distal catheter region having a contour which may be dynamically adjusted during use to conform to the contour of the atrium or other anatomical feature of interest.

Figure 6A:
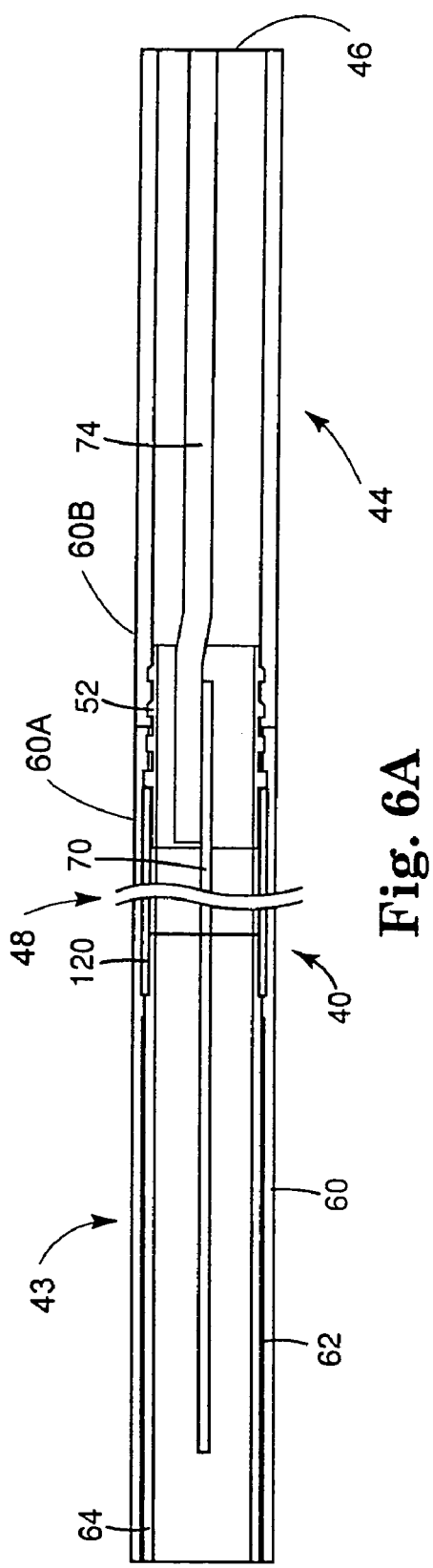
FIG. 6A is a cross-sectional view of a catheter employing a proximal steering mechanism in accordance with an embodiment of the present invention.
Figure 6B:
FIG. 6B is a cross-sectional view of the catheter shaft subassembly at a proximal section of the catheter shown in FIG. 6A.
Figure 6C:
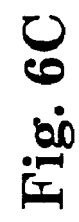
FIG. 6C is a cross-sectional view of the catheter shaft subassembly of the catheter depicted in FIG. 6A taken at a deflection region situated between the proximal section and an anchor section of the catheter shown in FIG. 6A.

Turning now to FIG. 6, there is illustrated an embodiment of a shape-adjustable catheter 40 employing a proximal steering mechanism in accordance with the principles of the present invention. It is noted that the catheter 40 shown in FIG. 6 is depicted in a linear or straight schematic configuration, without curvature indicated for purposes of clarity. According to this embodiment, catheter 40 is shown to include a proximal section 43, a deflection section 48, a pre-shaped section 44, and a distal tip 46. The shaft of catheter 40 at the proximal section 43 includes three layers. An outer layer 60 at the proximal section 43 is formed of a high durometer (e.g., 63 Shore D) PEBAX outer jacket having an outside diameter of 0.094 inches or 7 French, and an inside diameter of 0.062 inches. The proximal portion 43 of the sheath of catheter 40 further includes a braid layer 62 formed of eight strands of interwoven stainless steel ribbon, each with 0.001 inch by 0.003 inch cross-section. The braided ribbon 62 has a diameter of 0.009 inches. The braided ribbon 62 stiffens the proximal portion 43 of the catheter shaft, so it minimally deflects under normal steering loads. An inner core of the catheter sheath includes a tube 60 of polyetheretherketone (PEEK), having a diameter of 0.064 inches and an outer diameter of 0.078 inches.

At the distal end of the proximal shaft section 43 resides a flexible compression cage 120 that engages with the PEEK tube 64 and is embedded within low durometer (e.g., 35 Shore D) PEBAX 60a. The compression cage 120 is preferably formed from nitinol. The sheath section of catheter 40 that includes the compression cage 120 and low durometer PEBAX jacket 60a defines all or a substantial portion of the deflection region 48 of catheter 40. The combination of compression cage 120 and low durometer PEBAX jacket 60a provides for deflection of catheter 40 proximal to an anchor band 52 when tension is applied to a steering tendon connected to anchor band 52. The compression cage 120, as will be described in greater detail below, facilitates deflection of the steering portion of catheter 40 relative to a longitudinal axis of catheter 40, and resists axial compression along the catheter's longitudinal axis.

To vary the stiffness of the catheter 40, the bending properties of either the catheter shaft (e.g., durometer of the polymeric materials) or the pre-shaped section 44 (e.g., the diameter or cross-section of a pre-formed stylet) can be varied along its length. This could be done to tune the relative stiffness of the distal tip region in order to minimize the risk of trauma. Furthermore, to help the distal tip 46 stay in the coronary sinus while the sheath is slid forward, the pre-shaped section 44 can include a slight bend or "hook" near the distal tip 46 so that the catheter 40 is less likely to slip out of the ostium.

Figure 8A:
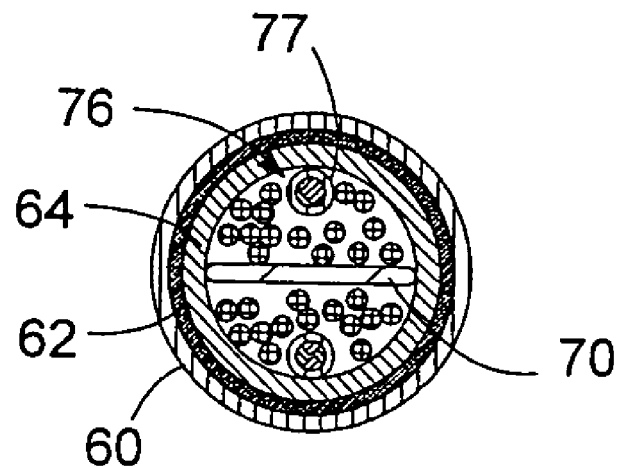
FIG. 8A is a more detailed cross-sectional view of a proximal section of the catheter shown in FIG. 6A according to an embodiment of the present invention.
Figure 8B:
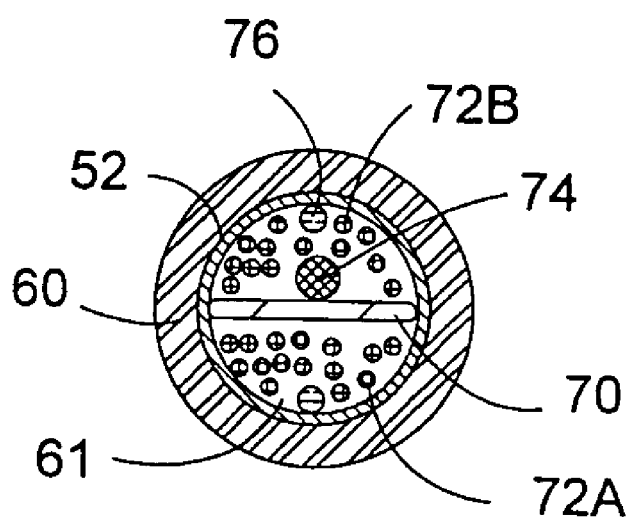
FIG. 8B is a more detailed cross-sectional view of the anchor section of the catheter shown in FIG. 6A according to an embodiment of the present invention.

As is further shown in FIG. 6A, an anchor band 52 is installed within at least a portion of the distal of opening of the compression cage 120. In one configuration, one or two stainless steel tendon wires 76, best seen in FIGS. 8A and 8B, are pre-affixed to the anchor band 52 prior to installation. One or two steering tendons 76 can be provided depending on whether the catheter 40 will steer in a uni-directional or bi-directional manner. Each steering tendon 76 is substantially enclosed within a lubricious tendon sheath 77, e.g., PTFE or similar material, that primarily serves to minimize friction between the tendon wire 76 and inner catheter wall. In one configuration, the tendon sheath 77 is bonded or otherwise affixed to the inner catheter wall, and the steering tendon 76 is slidably disposed within the tendon sheath 77. This serves to restrain the steering tendon 76 from undesired movements (e.g. radial deflections) while allowing the steering tendon 76 to axially slide within the catheter's sheath. In an alternate configuration, the tendon sheath 76 can be formed as a void in the PEEK tube wall.

It is preferable that the attachment point of the steering tendon(s) 76 to the metallic anchor band 52 be accomplished by welding or soldering. The anchor band 52 may then be embedded within the wall of the catheter during shaft lay-up. Alternatively, the anchor band 52 may be adhered at a later fabrication stage to the inner wall of the catheter shaft, such as by adhesive bonding or by hot melting the shaft material.

Attached to a distal end of the anchor band 52 is a hollow distal jacket section 60b formed of a low durometer PEBAX material, upon which an array of band electrodes (not shown) can be placed. The distal tip 46 of catheter 40 is typically a metal component that is affixed to the distal end of the PEBAX distal jacket 60b. The metal component at the distal end 46 of catheter 40 can be platinum, if used for ablation, or less expensive stainless steel, if no ablation is intended.

In one embodiment, the electrodes provided at the distal end of catheter 40 include twelve band electrodes arranged in a substantially linear array along the distal portion of catheter 40. A tip electrode may also be provided at the distal tip 46 of catheter 40. The band electrodes may be arranged so that there is space between the adjacent electrodes. In one configuration, the width of the band electrodes is 3 mm and the space between the electrodes is 4 mm. It is understood that the arrangement of band electrodes is not limited to a linear array and may take the form of other patterns. For example, a substantially linear array is preferred for certain therapeutic procedures, such as treatment of atrial fibrillation, in which linear lesions of typically 4-8 cm in length are desired. A linear array is more easily carried by the catheter 40 and also lessens the size of the catheter.

Temperature sensors for monitoring the temperature of the electrodes at various points along the distal portion of catheter 40 may also be provided. In one configuration, each band electrode has a temperature sensor mounted to it. Each temperature sensor provides a temperature signal which is indicative of the temperature of the respective band electrode at that sensor. In another embodiment, a temperature sensor is mounted on every other band electrode. In yet another configuration, every other electrode can have two temperature sensors.

The pre-shaped member 74 is formed of a resilient material capable of retaining a pre-formed shape upon removal of deformation forces acting thereon. The pre-shaped member 74 is preferably made of superelastic wire or ribbon material so that it readily straightens while being fed into the cardiac anatomy and then readily resumes its original pre-shaped configuration. In general, the configuration of pre-shaped member 74 is selected to approximate a given anatomical requirement. In addition, once the pre-shaped member 74 passes into a biological tissue cavity, such as the right atrium, for example, the shape of the distal portion of catheter 40 resumes its pre-formed configuration.

In the configuration illustrated in FIG. 6A, pre-shaped member 74 represents a stylet that resides within the catheter 40, and is preferably affixed to the distal tip 46 of catheter 40 to prevent migration of pre-shaped member 74 within the catheter 40 while in use. The pre-shaped member 74 may also be fixably attached to the anchor band 52 by means such as filling the anchor band 52 with an adhesive to trap the pre-shaped member therein. Attaching the pre-shaped member 74 in this way allows more effective torque transmission from the catheter's proximal shaft to the distal tip 46. It is noted that the desired pre-shape of the distal-end portion of catheter 40 may alternatively be imparted by heat-setting the polymer catheter shaft material at the distal end of catheter 40.

In one embodiment, pre-shaped member 74 is formed from superelastic nitinol wire which has been previously heated under constraint to permanently set the intended shape. The superelastic nitinol member, such as a stylet, is held in a fixture and heated to approximately 500° C. for about 15 minutes. The diameter of the nitinol stylet can be varied, such as by grinding, to tailor its bending stiffness where appropriate, such as to soften the distal tip section for minimizing trauma risk.

For simplicity, a pre-shaped stylet 74 can have a round cross-section over most of its length. In principle, however, pre-shaped stylet 74 could have other cross-section, such as a D-shaped, square or rectangular, or other shape depending largely upon the intended pre-shape and its desired bending characteristics. The pre-shaped stylet 74 can also be flattened or tapered where the stylet's proximal portion forms a joint with steering ribbon 70. It is appreciated that a single pre-shape will likely not be suitable for all patients. Therefore, it is likely that a family of several different pre-shaped stylets 74 would be available to the physician.

The steering ribbon 70 extends through at least of portion of the proximal section 43 and substantially all of the deflection section 48 of the catheter shaft. The width of steering ribbon 70 is preferably matched to that of the shaft lumen. As is best seen in FIGS. 8A and 8B, steering ribbon 70 has a width such that it contacts diametrically opposed sides of the sheath inner wall, thereby bisecting the lumen of the proximal and deflection sections 43, 48 of catheter 40. Sets of electrical wires 72A, 72B and are separated from one another by steering ribbon 70. An equal number of electrical wires 72 are preferably situated on either side of steering ribbon 70.

A pair of steering tendons 76, as is further shown in FIGS. 8A and 8B, is separated within the catheter's lumen by steering ribbon 70. In the proximal section 43 of the catheter's lumen, steering tendon(s) 76 are covered with a tendon sheath 77, such as by a coating of PTFE. It is noted that the steering tendon wire(s) 76 are not sheathed in the particular cross-section shown in FIG. 8B because the tendon(s) 76 are welded directly to the inner wall of the anchor band 52.

The steering ribbon 70 not only conveniently segregates the electrical wires, but it also forces the steering tendon(s) 76 to always reside along the same side as their attachment point(s) on the anchor band 52. If the later were not so, then it would be possible for the deflectable section 48 to deflect in an unintended direction or assume an unpredictable profile, such as the shape of the "S," instead of a semicircular arc or other shape that is intended. It is noted that if the steering ribbon 70 were eliminated, then steering profiles could be controlled by permanently affixing each steering tendon sheath 77 to the inner wall of the shaft lumen in order to prevent tendon wire migration. As shown, the steering ribbon 70 is deliberately thin for ease of bending, and preferably made of a resilient material, such as superelastic nitinol, so that it can withstand severe deflections due to steering without permanently deforming.

As is shown in FIGS. 6A and 8B, a proximal end portion of pre-shaped member 74 is joined with a distal-end portion of steering ribbon 70 within anchor band 52. As shown in FIGS. 6A and 8B, a lap joint between the steering ribbon 70 and pre-shaped member 74 is formed within the anchor band 52.

Figure 7A:
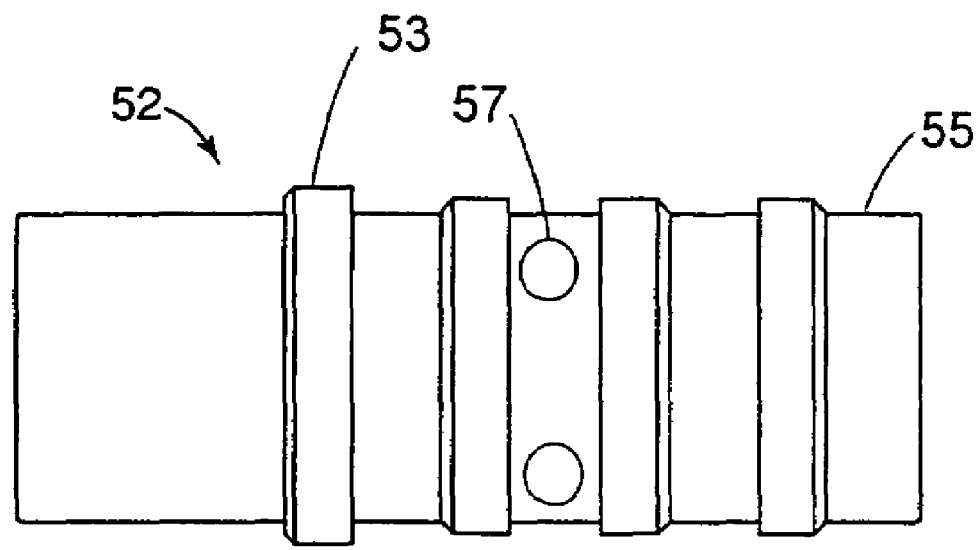
FIG. 7A is a side view of the anchor section of the catheter shown in FIG. 6A.
Figure 7B:
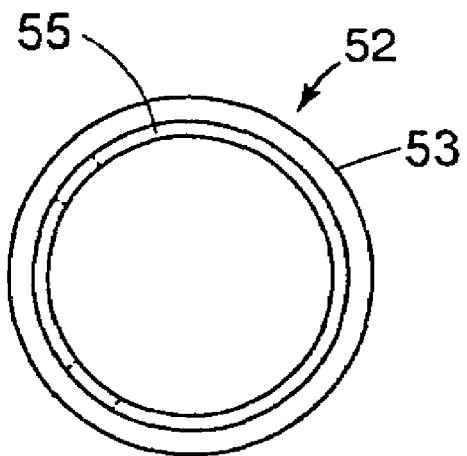
FIG. 7B is a cross-sectional view of the anchor section of the catheter shown in FIG. 6A.

The anchor band 52 can be formed from a stainless steel ring, and is typically affixed to the shaft wall material 60 of catheter 40. Side and front views of anchor band 52 are provided in FIGS. 7A and 7B. Anchor band 52 includes a main cylindrical portion 55 and a number of spaced annular rings or ribs 53. The anchor band 52 may also include one or more weep holes 57 that allow filling the anchor band with an adhesive during assembly. The steering tendon wire(s) 76 is preferably welded or soldered to the inner wall of the anchor band 52. The steering tendon axis is parallel to but offset from the longitudinal axis of the catheter shaft. Pulling the steering tendon 76 causes the shaft to deflect such that the pulled tendon 76 always follows the inside radius of shaft curvature.

To improve torque transmission of the overall catheter assembly, the remaining space within the anchor band 52 may be filled with an adhesive or other filler material, such as epoxy, cyanoacrylate, urethane, or other suitable filler material. Use of such an adhesive as a filler material within anchor band 52 also serves to maintain alignment between the preferred bending planes of the compression cage 120 and steering ribbon 70, thereby assuring steering uniformity.

The deflectable section 48 of catheter 40 is advantageously implemented to deflect in a predictable, selectable manner, while carrying the accompanying axial compressive load whenever a tensile load is applied to a steering tendon 76. Those skilled in the art readily appreciate the difficulty for an ordinary thin-wall deflectable structure to endure deformation forces associated with catheter manipulation without buckling or excessively wrinkling. Catheter 40 implemented in accordance with an embodiment of the present invention employs a compression cage 120 that allows for a desired level of catheter shaft flexibility at the deflection section 48 of catheter 40, while providing the requisite columnar support needed to prevent undesirable buckling due to excessive compressive axial loads.

Turning now to FIGS. 9A-9E, there are illustrated various embodiments of a compression cage 120 in accordance with the principles of the present invention. It is understood that a catheter 40 implemented in accordance with the present invention preferably incorporates compression cage 120 within the catheter structure, but in certain implementations, compression cage 120 may optionally be excluded.

With reference to FIGS. 9A-9E, various configurations of a support system or compression cage 120 are shown. In one configuration, shown in FIG. 9A, the compression cage 120 includes a flat-wire coil 126 and two substantially longitudinal struts 128. The struts 128 are diametrically opposed from each other and are welded, soldered, brazed, adhered, or otherwise attached to some or all loops of the coil 126. In another configuration, shown in FIG. 9B, the compression cage 120 includes a round-wire coil 130 and two substantially longitudinal struts 132. The struts 132 are diametrically opposed from each other and are welded, soldered, brazed, adhered, or otherwise attached to some or all loops of the coil 130.

Figure 9A:
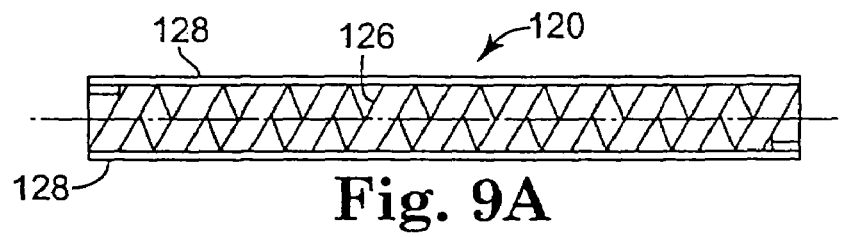
FIG. 9A is a view of a support system comprising a flat-wired coil and struts.
Figure 9B:
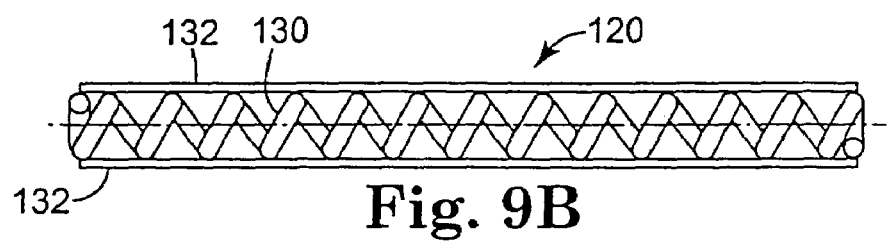
FIG. 9B is a view of a support system comprising a round-wire coil and struts.
Figure 9C:
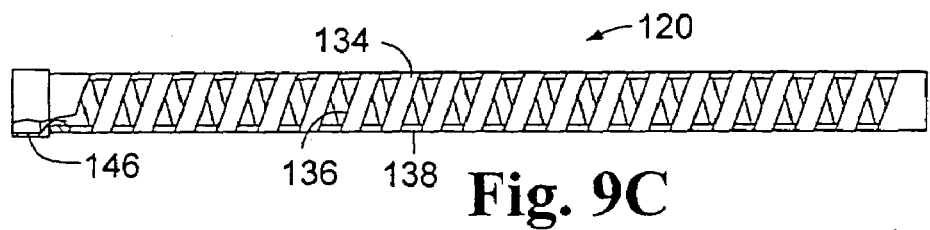
FIG. 9C is a view of a support system comprising a tubular member with an array of deep notches.
Figure 9D:
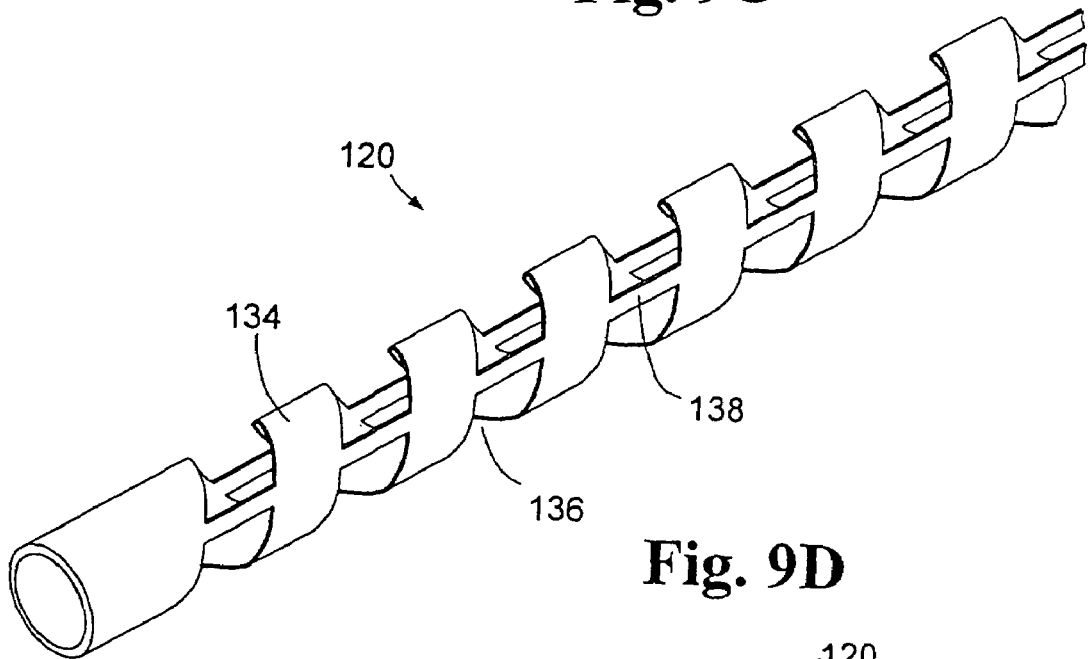
FIG. 9D is a perspective view of the support system shown in FIG. 9C.
Figure 9E:
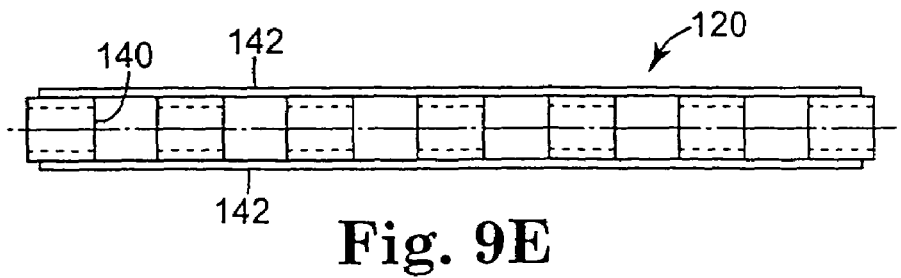
FIG. 9E is a view of a support system comprising a linear array of hollow rings connected with struts.

In another configuration, shown in FIGS. 9C and 9D, the compression cage 120 includes a substantially tubular member 134 with an array of deep notches 136 cut at a pitch angle. The material remaining between opposing notches 136 is thereby formed into a substantially helical structure with connecting struts 138. In yet another configuration, shown in FIG. 9E, the compression cage 120 includes a linear array of rings 140 and two substantially longitudinal struts 142 that interconnect the rings. The struts 142 are diametrically opposed from each other and are welded, soldered, brazed, adhered, or otherwise attached to each of the rings 140.

The primary function of the struts 128, 132, 138, 142 is to provide columnar strength to the compression cage 120. When a tensile load is applied to a steering tendon 76 to induce deflection of the distal-end region 44 of catheter 40, the reaction to the load is carried by the struts 128, 132, 138, 142 within the compression cage 120 and transferred into the relatively rigid proximal region 43 of catheter 40. The compression cage 120 deflects laterally most easily in a direction that is perpendicular to the plane in which a pair of opposing struts 128, 132, 138, 142 are located.

The support system 120 and anchor band 52 can be attached to the inner surface of the sheath within the deflection region 48, such as by melt-bonding, use of adhesives, or some other mechanical means. In an alternate and particularly useful configuration, the support system 120 is embedded within the walls of the sheath. Embedding the support system 120 within the catheter sheath serves to maximize the lumen diameter because there is only one "composite" wall having reduced thickness relative to the combined thickness that would result if the support system 120 were attached to an inner surface of the sheath walls.

The proximal end of the embedded support system 120 can be attached to the catheter using a union 146, best seen in FIG. 9C. An enlarged end of the union 146 fits over the distal end of the PEEK tube 64, and the narrowed end of the union 146 fits inside the support structure 120. The union 146 helps ensure that axial compressive loads carried by the support structure are reliably transferred to the proximal region 43 of the catheter sheath.

A tensile load produced by axial translation of a steering tendon 76 in the proximal direction causes the deflection region 48 to compress in the area of the support system 120 and to stretch in the area distal the support system 120. However, as previously mentioned, the reaction to the tensile load is carried by the struts 128, 132, 138, 142 within the support system 120 and is transferred into the relatively rigid proximal region 43 of the catheter sheath, thereby minimizing the associated compression and stretching of the deflection region 48 of the catheter sheath.

The support system 120 and other elements of catheter 40 described hereinabove may be configured as described in commonly owned U.S. Pat. Nos. 6,270,496; 6,585,718; 6,605,086; and 6,096,036, all of which are hereby incorporated herein by reference in their respective entireties.

As was discussed previously, a catheter 40 of the present invention may be employed in a variety of applications. In a configuration in which catheter 40 is implemented as an EP diagnostic catheter, catheter 40 is typically fed through a guiding catheter or introducer sheath and placed within the right atrium. The electrical leads from mapping electrodes located at the distal-end region of catheter 30 can be connected to an ECG monitor, and the ECG waveforms from adjacent electrode pairs can may be examined. Since the proportion of atrial ("A") signal relative to ventricular ("V") signal changes progressively throughout the atrium, ECG waveforms can be used to home in on the location of the coronary sinus ostium. It is noted that the coronary sinus resides in a region where the "A" and "V" signals are approximately equal in strength. Using both ECG and fluoroscopy feedback, the distal end of the EP diagnostic catheter 40 of the present invention would be readily manipulated into the coronary sinus, and then the guiding catheter or sheath would be made to track over the EP diagnostic catheter 40 and "deep seated" within the coronary sinus. If the sheath were equipped with an occlusion balloon, it could then be inflated to anchor it in place while the EP diagnostic catheter 40 is removed. At this point, an angiogram would typically be performed followed by implantation of a pacing lead.

An important advantage associated with the present invention is that CHF implant procedure times presently vary widely, and that an EP diagnostic catheter 40 of the present invention could be used as a "frontline" device to make the procedure more predictable. Instead of the present situation where the clinician is left to his own devices if the pre-shaped guide or sheath fails to locate the coronary sinus, the catheter 40 of the present invention in conjunction with a non-shaped guide or sheath would provide a consistent, reliable means of quickly locating the coronary sinus.

In another configuration, a catheter 40 according to the present invention can be employed as an ablation catheter. A particularly useful ablation treatment for patients with atrial fibrillation involves ablating tissue around a pulmonary vein orifice. This procedure, known as circumferential RF ablation, can be used to isolate the pulmonary veins from the left atrium. The procedure involves introducing the ablation catheter 40 into the left atrium, typically via transseptal catheterization. Proper catheter location within the left atrium can be confirmed by fluoroscopy or advanced ultrasonic means. Ablation is preferably performed by applying a combination of bipolar (band electrode to band electrode) and unipolar (band electrode to backplate, e.g., cutaneous ground patch) potential differences. These potential differences can be applied using multiphase RF energy delivery as well as sequential unipolar/bipolar RF delivery. The resulting unipolar and bipolar currents promote both lesion depth and lesion fill-in between band electrodes.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising:
   providing a sheath comprising:
      a proximal region having a stiffening braid;
      a deflection region adjacent to the proximal region and distal relative to the proximal region; and
      a distal-end region adjacent to the deflection region and distal relative to the deflection region, the distal-end region comprising:
         a shapeable region;
         an anchor region defined between the deflection region and the shapeable region;
         an anchor band within the anchor region;
         one or more steering tendons attached to the anchor band;
         a compression cage defining at least a substantial portion of the deflection region, the compression cage including a coil and two diametrically opposed longitudinal struts attached to loops of the coil; and
         a longitudinal axis;
   imparting a pre-established shape to the shapeable region; and
   applying axial force in a proximal direction at the anchor region using the one or more steering tendons so as to cause the deflection region to deflect relative to the longitudinal axis while the pre-established shape imparted to the shapeable region of the sheath is substantially maintained, wherein the deflection region deflects laterally in a direction that is perpendicular with respect to a projected plane formed by the two diametrically opposed longitudinal struts of the compression cage.

2. The method of claim 1, further comprising resisting axial compression along the longitudinal axis at the deflection region resulting from application of the axial force.

3. The method of claim 2, wherein resisting axial compression comprises urging deflection of the sheath laterally relative to the longitudinal axis of the sheath.

4. The method of claim 1, further comprising deforming the shapeable region to a substantially straightened configuration to facilitate movement of the sheath through vasculature, and resuming the shapeable region to the pre-established shape when unconstrained by the vasculature.

5. The method of claim 1, wherein imparting the pre-established shape comprises advancing a member through a lumen of the sheath and into the shapeable region, a distal region of the member assuming the pre-established shape when advanced into the shapeable region.

6. The method of claim 1, wherein the shapeable region comprises a pre-formed outer portion of the sheath.

7. The method of claim 1, wherein the shapeable region comprises a pre-formed outer member secured to the sheath.

8. The method of claim 1, wherein the pre-established shape of the shapeable region is imparted by a stylet having a pre-determined shape.

9. The method of claim 1, further comprising applying the axial force at the anchor region to cause a change in a bend angle at the deflection region while the pre-established shape of the shapeable region is substantially maintained.

10. The method of claim 1, wherein applying the axial force comprises applying the axial force in a direction offset relative to the longitudinal axis of the sheath.

11. The method of claim 1, wherein the sheath further comprises a steering ribbon extending at least from the proximal region to the deflection region of the sheath, the steering ribbon having a width sufficient to contact an inner surface of the sheath at two diametrically opposite locations of the inner surface of the sheath, and wherein the steering ribbon separates a first steering tendon from a second steering tendon of the one or more steering tendons.

12. The method of claim 11, further comprising steering the distal end of the sheath in two directional planes, wherein respective deflection planes of the compression cage and the steering ribbon are aligned to maintain steering uniformity.

13. The method of claim 1, wherein the anchor band includes a main cylindrical portion and a plurality of spaced annular rings.

14. The method of claim 13, further comprising:
inserting an introducer into a selected cardiac location;
guiding the sheath through the introducer; and
extending the shapeable region of the sheath beyond a distal end of the introducer thereby allowing the shapeable region to assume the pre-established shape.

15. The method of claim 1, wherein the proximal region is maintained in shape during deflection of the deflection region.

16. The method of claim 15, wherein sensing cardiac signals comprises mapping cardiac tissue.

17. The method of claim 1, further comprising delivering energy from the shapeable region of the sheath.

18. The method of claim 17, wherein delivering energy comprises delivering energy sufficient to ablate cardiac tissue.

\* \* \* \* \*